United States Patent
Happer et al.

(10) Patent No.: US 8,456,161 B2
(45) Date of Patent: Jun. 4, 2013

(54) POLARIZING NUCLEI SOLIDS VIA SPIN TRANSFER FROM AN OPTICALLY-PUMPED ALKALI VAPOR

(75) Inventors: William Happer, Princeton, NJ (US);
Kiyoshi Ishikawa, Princeton, NJ (US);
Brian Patton, Princeton, NJ (US);
Yuan-Yu Jau, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 471 days.

(21) Appl. No.: 12/439,846

(22) PCT Filed: Sep. 5, 2007

(86) PCT No.: PCT/US2007/019492
§ 371 (c)(1),
(2), (4) Date: Aug. 12, 2010

(87) PCT Pub. No.: WO2008/030545
PCT Pub. Date: Mar. 13, 2008

(65) Prior Publication Data
US 2010/0301853 A1  Dec. 2, 2010

Related U.S. Application Data (60) Provisional application No. 60/842,325, filed on Sep. 5, 2006.

(51) Int. Cl.
*G01V 3/00* (2006.01)
(52) U.S. Cl.
USPC .......................................... 324/309; 324/300
(58) Field of Classification Search
USPC ................... 324/300–322; 62/637, 919, 925, 62/55.5
See application file for complete search history.

(56) References Cited

U.S. PATENT DOCUMENTS

| | | |
|---|---|---|
| 3,133,199 A | 5/1964 | Horton |
| 5,617,859 A | 4/1997 | Souza et al. |
| 5,809,801 A | 9/1998 | Cates, Jr. et al. |

(Continued)

FOREIGN PATENT DOCUMENTS

GB  1081724 A  8/1967

OTHER PUBLICATIONS

Wolber et al., "Generating highly polarized nuclear spins in solution using dynamic nuclear polarization" Nuclear Instruments and Methods in Physics Research A 173-181 (2004).

(Continued)

*Primary Examiner* — Brij Shrivastav
(74) *Attorney, Agent, or Firm* — Porzio, Bromberg & Newman, P.C.

(57) ABSTRACT

The present invention relates to a method and system for polarizing a solid compound of interest via spin transfer from an optically-pumped alkali vapor. In one embodiment, the method provides a cell which contains a solid compound as well as pure alkali metal and some amount of buffer gas. The cell is heated to vaporize some of the pure alkali. Resonant laser light is passed through the cell to polarize the atomic vapor, a process known as "optical pumping." Optical pumping can transfer order from photons to atoms, causing a buildup of vapor atoms in one angular momentum state. This vapor polarization is then transferred through the surface of the solid compound in order to polarize the nuclei in the bulk of the compound. This can produce nuclear polarizations in the sample many times larger than the limit set by thermal equilibrium. The method can be used in nuclear magnetic resonance (NMR) or magnetic resonance imaging (MRI).

48 Claims, 6 Drawing Sheets

U.S. PATENT DOCUMENTS

| | | |
|---|---|---|
| 6,125,654 A | 10/2000 | Honig |
| 6,295,834 B1 * | 10/2001 | Driehuys .................. 62/637 |
| 6,318,092 B1 | 11/2001 | Happer et al. |
| 6,430,960 B1 * | 8/2002 | Driehuys .................. 62/637 |
| 6,566,875 B1 * | 5/2003 | Hasson et al. ............ 324/309 |
| 6,919,770 B2 | 7/2005 | Happer et al. |
| 7,038,450 B2 * | 5/2006 | Romalis et al. ........... 324/304 |
| 7,102,451 B2 | 9/2006 | Happer et al. |
| 7,145,333 B2 * | 12/2006 | Romalis et al. ........... 324/304 |
| 7,287,390 B2 * | 10/2007 | Bolam ...................... 62/55.5 |
| 7,287,391 B2 * | 10/2007 | Bolam ...................... 62/55.5 |
| 7,521,928 B2 * | 4/2009 | Romalis et al. ........... 324/304 |
| 8,035,376 B2 * | 10/2011 | Bolam ...................... 324/304 |
| 8,212,556 B1 * | 7/2012 | Schwindt et al. ......... 324/304 |
| 2002/0058869 A1 | 5/2002 | Axelsson et al. |
| 2010/0327862 A1 * | 12/2010 | Nagasaka ................ 324/244.1 |

* cited by examiner

POLARIZING NUCLEI SOLIDS VIA SPIN TRANSFER FROM AN OPTICALLY-PUMPED ALKALI VAPOR

STATEMENT OF GOVERNMENT FUNDED RESEARCH

This work was supported by the Air Force Office of Scientific Research FA9550-04-1-0199. Accordingly, the Government has certain rights in this invention.

BACKGROUND OF THE INVENTION

1. Field of the Invention

The present invention relates to a method and system for polarizing the nuclei of a solid compound via spin transfer from an optically-pumped alkali vapor and use of the method in nuclear magnetic resonance (NMR) or magnetic resonance imaging (MRI).

2. Description of the Related Art

Since the discovery of nuclear magnetic resonance (NMR), attempts have been made to increase NMR signals by artificially aligning nuclear spins to a higher degree than the statistical limit set by thermal equilibrium in a magnetic field. This is motivated by the fundamentally low sensitivity of nuclear magnetic resonance. Even in the large magnetic fields used in magnetic resonance imaging (MRI), the interaction energies between atomic nuclei and the external field are dwarfed by thermal energies. In a magnetic field of 1.5 Tesla (a value commonly used for MRI) the coupling energy between a proton spin and the external field is:

$$\Delta E = \hbar \gamma B_{ext} \approx 2.6 \times 10^{-7} \text{ eV} \quad (1)$$

roughly five orders of magnitude smaller than thermal energy at room temperature. Here $\Delta E$ refers to the difference in energy between a spin-up (aligned with the external field) and a spin-down (anti-aligned) proton; $\hbar$ is the reduced Planck constant; $\gamma$ refers to the proton's gyromagnetic ratio (roughly 42.6 MHz/Tesla); and $B_{ext}$ refers to the magnitude of the externally applied field. Because this coupling is so small, the thermally-induced polarization, given by:

$$P_o \equiv \frac{N_\uparrow - N_\downarrow}{N_\uparrow + N_\downarrow} = \tanh\left(\frac{\gamma \hbar B_0}{2 k_B T}\right) \quad (2)$$

is only $5 \times 10^{-6}$. The polarization is by definition a measure of the difference in population between aligned nuclear spins ($N_\uparrow$) and anti-aligned spins $N_\downarrow$, normalized by their sum. Here $k_B$ refers to Boltzmann's constant. Accordingly, $k_B T$ is the thermal energy at temperature T. This result implies that only 5 nuclei per million are visible to the MRI instrument. Solutions for increasing this number, namely lowering the temperature dramatically or increasing the magnetic field, are prohibited in most circumstances such as diagnostic medical imaging. Accordingly, much research has focused on ways to polarize nuclei above this equilibrium limit.

Figure 1A:
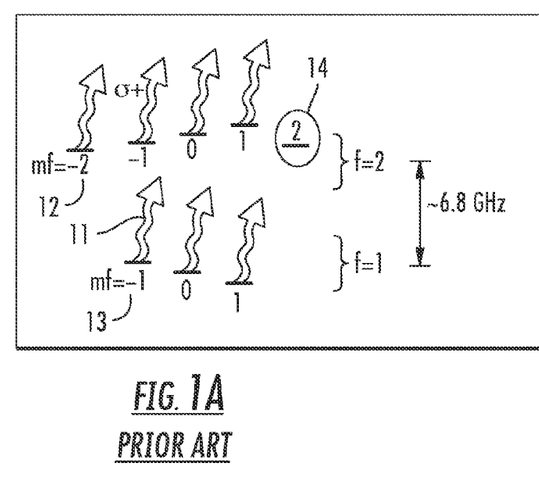
FIG. 1A is an $^{87}$Rb level diagram which illustrates D1 pumping with circularly polarized light in low magnetic field.

It has been found that angular momentum can be transferred effectively from circularly-polarized light to atoms via resonant absorption, as described in A. Kastler, Science 158, 214 (1967). Since nuclei have transitional energies which are inaccessible by optical photons, one common scheme for polarization transfer is to pump electronic transitions with circularly-polarized light and then rely upon these polarized electrons to carry angular momentum to the nuclei of interest, which may or may not be within the same atom. Nuclei within the same atom can be polarized by the atom's own hyperfine coupling, which is the fundamental interaction between the electron and the nucleus. FIG. 1A is a $^{87}$Rb level diagram which illustrates D1 pumping with circularly polarized light in low magnetic field. Because of the strong hyperfine coupling between the electron and the nucleus, states are represented in the total angular momentum basis $|f, m_f\rangle$. Light absorption promotes the atom to one of the excited $^2P_{1/2}$ states (not shown). The hyperfine splitting of 6.8 GHz is shown between the f=1 and f=2 ground-state sublevels (13 and 12, respectively). Because of conservation of angular momentum, σ+ light shown by arrows 11 cannot be absorbed by the maximum angular momentum sublevel 14. Spontaneous decay from the excited state (not shown) repopulates the ground states 12 and 13 evenly, so the atoms are soon concentrated in the only state which is not depopulated which is the |2,2⟩ state 14 as circled in FIG. 1A.

Figure 1B:
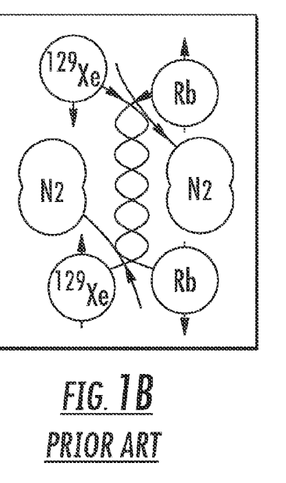
FIG. 1B is a schematic diagram of spin transfer from an $^{87}$Rb electron to a $^{129}$Xe nuclei through spin exchange in a van der Waals molecule.

Nuclei in external atoms can be polarized through collisional interactions with the polarized alkali electron, shown in FIG. 1B. This process is called spin-exchange optical pumping (SEOP), and has been used successfully to polarize noble gas nuclei, as described in W. Happer, Annales de Physique 10, 645 (1985); J. C. Leawoods, D. A. Yablonskiy, B. Saam, D. S. Gierada, and M. S. Conradi, Concepts in Magnetic Resonance 13, 277 (2001); and S. Appelt, A. B.-A. Baranga, C. J. Erickson, M. V. Romalis, A. R. Young, and W. Happer, Physical Review A 58, 1412 (1998). Spin transfer from $^{87}$Rb electron to a $^{129}$Xe nuclei occurs through spin exchange within a Rb—Xe van der Vaals molecule. SEOP can produce noble gases with nuclear polarizations approaching 100%, increasing the NMR signals of these gases by four to five orders of magnitude over the thermal limit, as described in B. Chann, E. Babcock, L. W. Anderson, T. G. Walker, W. C. Chen, T. B. Smith, A. K. Thompson, and T. R., Gentile, Journal of Applied Physics 94, 6908 (2003) and I. C. Ruset, S. Ketel, and F. W. Hersman, Physical Review Letters 96 (2006). Such polarizations are useful in many applications, ranging from precise atomic physics to spectroscopy to medical diagnostics and imaging.

Additional mechanisms of spin transfer have been implemented in research, including direct optical pumping of semiconductors and crystals, photo-induced production of polarized radicals in biomolecules, parahydrogen-induced polarization (PHIP), and dynamic nuclear polarization (DNP) techniques.

Although spin-exchange optical pumping has been remarkably successful, its only implementation has been to polarize the nuclei of noble gases. Yet because of their very nature, noble gases are largely inert which makes polarized noble gases unsuitable for the study of chemical interactions. Further, because of their low density in gaseous phase, it is difficult to generate large masses of the polarized materials. In the case of xenon, one conventional solution to this problem is to use a continuous-flow system with a cold trap which freezes the polarized gas. Once a large enough mass of xenon has been collected in the cold trap, it can be thawed and used in experiment. However, this freezing/thawing cycle can be an additional source of polarization loss, as described in N. N. Kuzma, B. Patton, K. Raman, and W. Happer, Physical Review Letters 88, 147602 (2002).

Another technique known as dynamic nuclear polarization (DNP) can be used to polarize nuclei in a solution sample, but this process requires special paramagnetic agents to be synthesized and admixed with the sample, as described in J. H. Ardenkjaer-Larsen, B. Fridlund, A. Gram, G. Hansson, L. Hansson, M. H. Lerche, R. Servin, M. Thaning, and K. Golman, Proceedings of the National Academy of Sciences of the United States of America 100, 10158 (2003). The mixture must then be cooled to 4 kelvin in a high magnetic field and irradiated with high-power microwave radiation to transfer electron spin polarization to the nuclear spins. The sample must then be thawed to room temperature very rapidly to prevent longitudinal spin relaxation from destroying the nuclear polarization. Finally, the paramagnetic polarization agent must be removed from the sample before it can be used in MRI or NMR.

It is desirable to provide a nuclear polarization technique which polarizes large amounts of a solid compound of chemical interest while still relying upon angular momentum transfer from an optically pumped alkali vapor, since optical pumping is an inexpensive and experimentally simple process.

SUMMARY OF THE INVENTION

The present invention relates to a method and system for polarizing a solid compound of interest via spin transfer from an optically-pumped alkali vapor. In one embodiment, the method involves a cell which contains a solid compound, a pure alkali metal, and possibly some amount of buffer gas. The cell is heated to vaporize some of the pure alkali. Resonant laser light is passed through the cell to polarize the atomic vapor, a process known as "optical pumping." Optical pumping can transfer order from photons to atoms, causing a buildup of vapor atoms in one angular momentum state. This vapor polarization is then transferred to the nuclei of the compound when vapor atoms collide with the solid surface. This can produce nuclear polarizations in the sample many times larger than the limit set by thermal equilibrium. The method can be used in nuclear magnetic resonance (NMR) or magnetic resonance imaging (MRI).

Though there are a variety of mechanisms through which the vapor polarization can be transferred to the compound, it has been shown that this process can happen spontaneously, without the need for external radiofrequency or microwave excitation of the sample. The mechanism can be effective at optical pumping temperatures. This avoids the technical challenge of cryogenics or rapid temperature cycling, experimental necessities which inhibit large polarizations in conventional techniques such as dynamic nuclear polarization (DNP). Magnetic field cycling is also unnecessary. The nuclei in the compound are polarized passively simply by being in contact with the optically-pumped vapor.

It may also be possible to increase the rate of spin transfer from the vapor to the solid by exposing the sample to microwave power at a frequency near the difference between the electron and nuclear Larmor frequencies at the applied magnetic field. The use of alkali vapor optical pumping provides a practical way to carry angular momentum into a spin system since alkali metals have low melting points and high vapor pressures, and when vaporized they exist as a monatomic gas. Accordingly, a large ensemble can interact with the photons without molecule or bulk crystal effects. Electron transitions in the alkalis can easily be excited with conventional lasers, including inexpensive high-power diode lasers. Alkali electrons can interact strongly with other atoms and nuclei, so their spin polarization can easily be transmitted.

The invention will be more fully described by reference to the following drawings.

DETAILED DESCRIPTION

Reference will now be made in greater detail to a preferred embodiment of the invention, an example of which is illustrated in the accompanying drawings. Wherever possible, the same reference numerals will be used throughout the drawings and the description to refer to the same or like parts.

Figure 2:
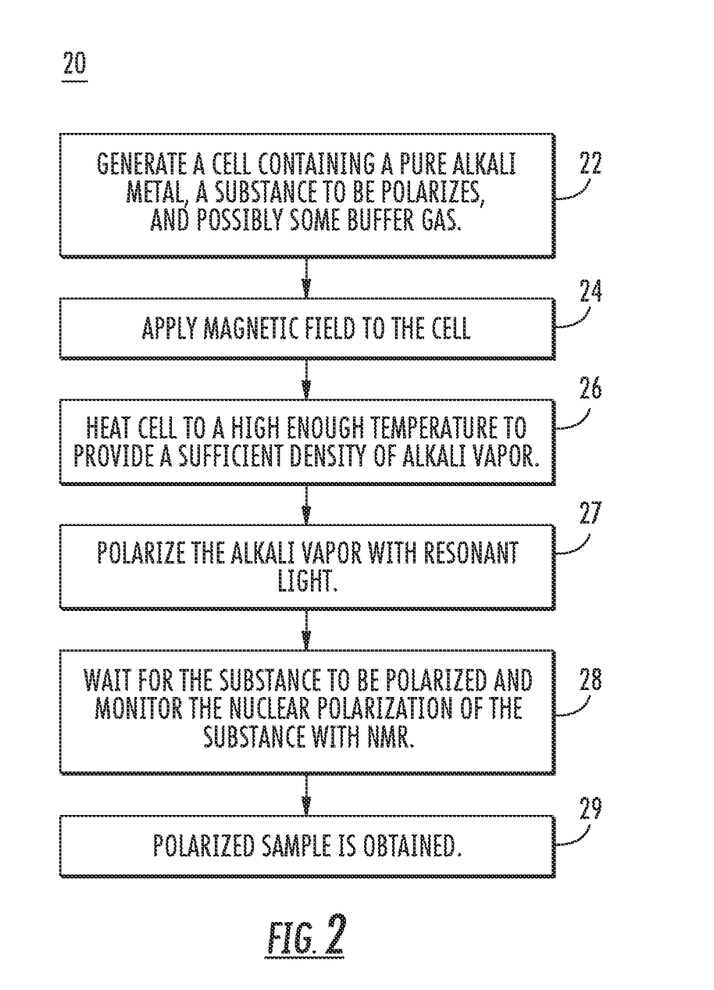
FIG. 2 is a flow diagram of a method for obtaining a polarized compound in accordance with the teachings of the present invention.

FIG. 2 is a flow diagram of a method for obtaining a polarized compound 20 in accordance with the teachings of the present invention. In block 22, cells are generated which contain a pure alkali metal, a substance to be polarized, and possibly a buffer gas intended to facilitate optical pumping. The substance to be polarized can be a salt which contains the same or a different alkali metal than the pure alkali metal which is in the cell. Example alkali salts include NaCl, CsH, CsCl, and CsF. Alternatively, the substance to be polarized can be an element or compound which does not contain alkali atoms, for example silicon. Preferably, the substance to be polarized is a solid. In one embodiment, the cell contains an alkali salt on its inner surface and a droplet of alkali metal in elemental form to produce an alkali vapor. Suitable buffer gases include nitrogen and hydrogen.

In block 24, a magnetic field is applied to the cell. The magnetic field can be a high field in which the Zeeman splitting of the element's electron states is larger than the hyperfine splitting between its valence electron and nucleus. Alternatively, the magnetic field can be a low field in which the Zeeman splitting of the element's electron states is smaller than the hyperfine splitting.

In block 26, the cell is heated. The cell can be heated to provide a desirable density of alkali vapor.

In block 27, the alkali vapor is polarized with resonant laser light. In one embodiment using a low magnetic field <~1 kG, polarized light is used. Alternatively, in another embodiment, using a high magnetic field, the light can either be polarized or unpolarized, since the large Zeeman splitting of the electron states ensures that only one Zeeman sublevel is depopulated, regardless of the helicity of the light. At low magnetic fields, the frequency "spread" of the ground-state sublevels is determined by the hyperfine splitting—6.8 GHz for Rb, as shown in FIG. 1A. At high magnetic fields, the alkali electron experiences a very strong coupling to the magnetic field, which means that the energy difference between a spin-up and a spin-down electron is (in frequency units) 260 GHz (at a field of 9.4 T), as shown in FIG. 3. At low fields, a diode laser has a broad enough frequency spectrum that all sublevels can be excited. To ensure that all the atoms are trapped in one particular sublevel, polarized light is used then atoms get trapped in the one sublevel (14) which can not absorb light of that polarization (helicity). At high magnetic fields, the two sets of sublevels are separated by such a large frequency range that a laser can excited all of them with $m_s=+\frac{1}{2}$ (for σ– light) or all the sublevels with $m_s=-\frac{1}{2}$ (for σ+ light), but not both at the same time. Accordingly, at high fields, the light does not really need to be polarized, since any light of the incorrect polarization passes through the cell unabsorbed.

In one embodiment, circularly polarized laser light composed of optical photons with angular momentum±1 in units of $\hbar$ can be used. The laser optical pumping light can be at a D1 transition or D2 transition of the alkali vapor. The pumping light is tuned to an electronic transition of the vapor, such as the D1 or D2 line of the alkali, referring to the $^2S_{1/2} \rightarrow {}^2P_{1/2}$ and $^2S_{1/2} \rightarrow {}^2P_{3/2}$ valence electron transitions, respectively.

In one embodiment, circularly-polarized laser light can be used to polarize the vapor, which can then transfer its angular momentum to the bulk of the salt through interactions with the compound's surface layer. The spin excess can then diffuse through the compound, polarizing the bulk of the salt nuclei.

In one embodiment, during or after block 27, the cell is exposed to microwave power at a frequency near the difference between the electron and nuclear Larmor frequencies at the applied magnetic field. In block 28, a time is waited for the substance to be polarized and then the nuclear polarization of the substance is monitored with NMR. In block 29, a polarized sample is obtained.

Alkali compounds are preferable because they tend to have long longitudinal relaxation times ($T_1$'s), such that they can retain this non-equilibrium polarization for many minutes after the optical pumping process. The alkalis have biological interest because their salts are generally non-toxic and their ions play a vital role in biological functions, such as cell communication via sodium and potassium ion channels. It is believed that spin transfer from an alkali vapor to an alkali salt is more efficient than to a different compound, since some spin transfer mechanisms may rely upon a matching of nuclear energy levels between the vapor atoms and the atoms in the bulk.

Figure 3A:
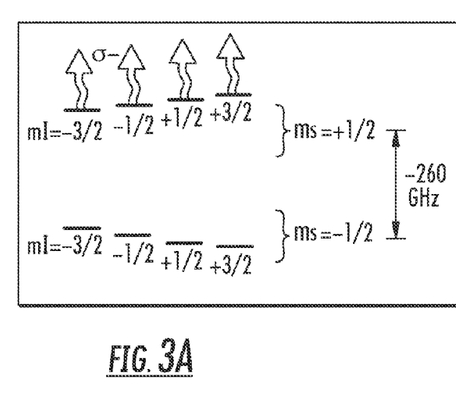
FIG. 3A is an $^{87}$Rb level diagram illustrating high-field optical pumping at 9.4 tesla with σ− light.
Figure 3B:
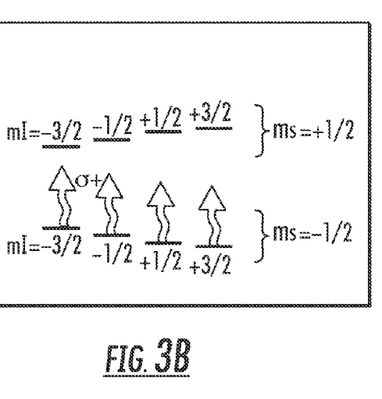
FIG. 3B is an $^{87}$Rb level diagram illustrating high-field optical pumping at 9.4 tesla with σ+ light.

Possible spin-transfer mechanisms between the vapor and the compound include: (i) direct atom exchange from the vapor to the salt; (ii) nuclear dipole-dipole interactions between absorbed atoms from the vapor and alkali atoms in the compound; (iii) spin-exchange interactions between vapor-phase electrons and nuclei in the salt; (iv) injection of polarized vapor electrons into the conduction band of the compound; (v) polarization of electron-filled lattice defects ("f-centers") by the vapor; or any of a variety of conventional physical mechanisms. Mechanisms (i) and (ii) both rely upon nuclear polarization within the alkali vapor itself which is then transferred to the solid of interest. Though this is a potential mechanism at low magnetic fields (≲0.1 tesla), it is quite difficult to polarize the vapor nuclei at high fields because of magnetic decoupling. At low fields the vapor atoms can be described in the $|f,m_f\rangle$ basis because the electron and nucleus are strongly coupled; this is the condition shown in FIG. 1A. At high magnetic fields, the electron spins are coupled much more strongly to the external magnetic field than to the nuclei, meaning the appropriate basis is the "decoupled" one: $|m_I,m_s\rangle$. As a consequence of this decoupling, optical pumping at high magnetic fields can polarize the electron states of the vapor, but cannot substantially affect the nuclear states, as shown in FIGS. 3A-3B. Ground-state atoms are excited to the $^2P_{1/2}$ state (not shown). Because the Zeeman splitting of the electron energies is much greater than the hyperfine splitting, the appropriate basis for the vapor atoms is the decoupled basis $|m_I,m_s\rangle$. The frequency and the wavelength of the pumping light can be changed to select which electron states are depopulated, but since all hyperfine sublevels of a given electron orientation tend to be pumped equally, the nuclear populations remain unchanged. In some circumstances, a degree of nuclear polarization can be produced in the vapor through alkali—buffer-gas collisions. Moreover, it is possible to produce nuclear polarization in the vapor through optical pumping of weakly-absorbing "forbidden" transitions, in which the value of $m_s$ doesn't change but the value of $m_I$ changes by one unit of $\hbar$.

Mechanism (iii) is akin to the interaction which allows for polarization transfer to noble gas nuclei in conventional spin exchange optical pumping (SEOP) as described in U.S. Pat. No. 6,919,770 hereby incorporated by reference into the present application. Mechanism (iv) can occur during impact of a vapor atom onto the salt surface; if the collision occurs with sufficient energy, the polarized electron of the vapor atom can be injected directly into the conduction band of the salt crystal. Alternately, absorbed metal atoms on the crystal could be optically pumped directly, promoting their electrons into the conduction band of the compound. Mechanism (v) provides experimental conditions which are favorable for the formation of f-centers as described in N. F. Mott and R. W. Gurney, Electronic Processes in Ionic Crystals, The International Series of Monographs on Physics (Clarendon Press, Oxford, 1948), 2nd ed., hereby incorporated by reference into the present application.

Whatever the interaction which transfers angular momentum from the vapor to the salt, some mechanism of spin diffusion is needed to propagate that polarization into the bulk of the crystal faster than the longitudinal relaxation processes can destroy it. The process by which this occurs is unknown. Conduction-band electrons may play a role in spin diffusion, or alternatively spin polarization could be transmitted in the crystalline salt is by f-centers, which are known to decrease longitudinal relaxation times of crystal nuclei, as described in N. Bloembergen, Physica 15, 386 (1949), hereby incorporated by reference into the present application, and could physically diffuse themselves, acting as carriers of the polarization. Nuclear dipole-dipole spin diffusion also contributes to the propagation.

Referring to FIG. 2, in block 28, the nuclear polarization of the substance is monitored during the time waiting for the substance to be polarized. For example, the substance can be monitored with microwave RF irradiation of the sample, nuclear magnetic resonance (NMR), atomic or SQUID (superconducting quantum interference device) magnetometry, and/or optical probing, such as by Faraday rotation. The waiting time should be larger than the nuclear relaxation time of the substance. In block 29, a polarized sample is obtained.

Figure 4:
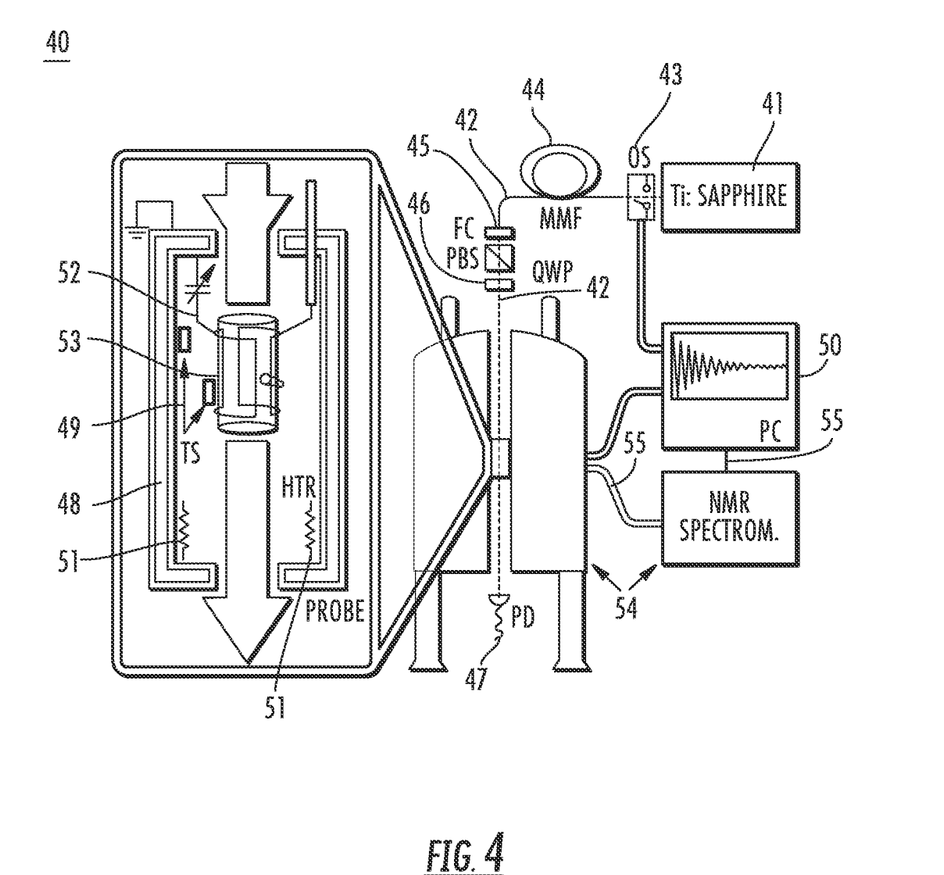
FIG. 4 is a schematic diagram of a system for obtaining a polarized compound.

Method 10 can be used for increasing nuclear polarization of a compound above the level set by a thermal equilibrium and enhancing its nuclear magnetic resonance (NMR) signal. Method 10 can be used for creating hyperpolarized compounds for use in NMR spectroscopy, in vivo or in vitro medical diagnostics, such as magnetic resonance imaging (MRI), or chemical identification. In these applications, the hyperpolarized compound can be extracted from the cell and separated from the alkali metal and used in MRI or NMR diagnostics FIG. 4 is a schematic diagram of a system for obtaining a polarized compound 40 in accordance with the teachings of the present invention. Laser 41 generates pumping light 42. For example, the laser 41 can be a Ti:Saph laser generating D1 pumping light. Pumping light 42 is routed through optical shutter (OS) 43 and into multimode fiber (MMF) 44. At output of multimode fiber (MMF) 44, pumping light 42 is polarized by the beam-splitter cube 45 and quarter-wave plate 46. Photodiode (PD) 47 verifies optical absorption. Temperature sensor 48 is used to measure probe temperature. Temperature sensor 49 is used to measure cell temperature. The probe temperature and cell temperature are stored at personal computer PC 50. Resistive heater 51 is controlled by PC 50 and is used to regulate the probe temperature. Cell 51 is supported in NMR coil 52. NMR spectrometer 54 is used to take NMR spectra data 55 of cell 50. NMR spectra data 55 is recorded in PC 50.

The invention can be further illustrated by the following examples thereof, although it will be understood that these examples are included merely for purposes of illustration and are not intended to limit the scope of the invention unless otherwise specifically indicated. All percentages, ratios, and parts herein, in the Specification, Examples, and Claims, are by weight and are approximations unless otherwise stated.

A. Cell Preparation

For this experiment, cells were fabricated which contained a uniform film of cesium hydride on the inner walls as well as a droplet of pure cesium metal to provide the alkali vapor. Pyrex cells, roughly 0.5 in diameter by 1.5 in long with optical windows were attached to a glass string, which was then connected to a vacuum manifold. A breakseal ampoule of cesium (Chemetall GmbH) was attached to the string, ultimately providing both forms of cesium. The cells were evacuated with a turbomolecular pump while being baked in an oven at 350° C. for several days until the residual pressure (as measured by a cold cathode gauge positioned at the pump inlet) fell below ~5×10$^{-8}$ Torr. The cells were then cooled to room temperature and the ampoule breakseal was broken with a glass-encapsulated magnetic hammer. Cesium was transferred into the cells by distillation with a low flame. Care was taken to ensure that the cesium did not flow into the cells as large droplets, but rather condensed as a uniform film on the cell walls. Cesium which condensed on the optical windows was removed by gentle heating. When the cesium film in each cell was deemed thick enough, the remaining metal was chased into the far end of the glass string and the manifold was pressurized with ~700 Torr $H_2$ gas. Because the reaction rate of cesium with hydrogen is quite low at room temperature, the cells had to be heated in order to produce a CsH film. This was accomplished by placing a smaller oven around the cells and baking them at 150° C. for more than 12 hours. Since the excess cesium metal remained in the end of the string outside the oven, it reacted very little. Once the reaction in the cells was complete (judged by the change in appearance of the film), the string was cooled down and evacuated once again so that additional layers of cesium could be deposited in the cells. This process of building up a pure cesium film and reacting it with $H_2$ gas was performed a total of three times, resulting in a thick film of CsH on the cell walls. The string was then evacuated once more and a droplet of pure cesium was loaded into the stem of each cell in the same manner as before. The cells were filled with varying amounts of $N_2$ as a quenching gas. Finally each cell was removed from the string by softening the stem with a torch and pulling off the cell, forming a permanent seal. It should be noted that cells with nitrogen pressures of 20 Torr and below tended to form a blue film of cesium metal over the hydride film. Heat from this sealing process invariably created some cesium vapor which was able to diffuse freely throughout the cell at such low pressures.

Cesium/cesium deuteride (CsD) cells were also made in an identical manner, with deuterium ($D_2$) gas substituted for $H_2$.

B. Experimental Setup

Nuclear magnetic resonance (NMR) data were taken in a 9.4 Tesla superconducting magnet with a NMR spectrometer, as shown in FIG. 4. Such high magnetic fields are generally used to achieve sufficient signal-to-noise in the $^{133}$Cs NMR signal. Free induction decays (FID's) were recorded on a Yokogawa DL708E oscilloscope and subsequently uploaded to a PC for data processing.

Because of the long $T_1$ of 133Cs in cesium hydride, NMR spectra were recorded and averaged at a delay of 180 s or longer. The NMR frequency of pure cesium metal was measured to be 53.15 MHz at this field; the frequency of 133Cs nuclei in CsH was 52.39 MHz. Cells were placed in a PTFE holder which supported an NMR coil in the "saddle" configuration. The coil was soldered to an NMR tank circuit and tuned to the appropriate resonance (here CsH) with variable capacitors. This NMR probe was housed in an oven which was heated with a counter-wrapped resistive wire; the magnetic field produced by this heating circuit was less than 0.05 ppm at the NMR coil. The temperatures of the oven and the cell were monitored by two resistive thermal devices (RTD's) whose readings were recorded on the PC concurrently with the NMR spectra. The oven was heated to 130-170° C. to ensure a sufficient cesium vapor density for optical pumping.

The laser system used was a Coherent 899-29 Titanium:Sapphire ring laser, pumped with a Coherent Verdi-10W laser at 532 nm. The cesium D1 transition (at 895 nm) was chosen for optical pumping. The Ti:Saph laser output power at this wavelength was approximately one watt. Since this experiment was performed at high magnetic field, direct manipulation of the nuclear states could not be achieved via optical pumping; only the electron states of the vapor could be polarized. The D2 transition (852 nm) could be expected to yield quantitatively similar results. An optical shutter was placed at the output of the Ti:Saph laser; it was controlled by the computer for long-term subtraction averaging (described below). The beam was then launched through a multimode optical fiber (ThorLabs) and directed axially down the bore of the magnet. A polarizing beam-splitter cube and a variable-angle quarter-wave plate were placed at the output of the fiber. The power of the circularly-polarized light striking the cell was measured to be 150-200 mW. Absorption by the vapor could be verified before each experiment by monitoring the signal from a photodiode, whose output was fed into a lock-in amplifier synchronized with a chopper placed in the beam path. The chopper was removed during the optical pumping experiment to allow full laser power.

C. Experimental Procedure

Each cell was placed in the NMR probe, which was then inserted in the magnet and heated to the target temperature. Once the temperature of the probe had equilibrated (usually 2-3 hours), the laser was tuned to the desired optical resonance (roughly 334940 HGz for σ− light, 335290 GHz for σ+ light) and the wave plate was rotated to the appropriate angle. The optimum transition frequencies varied slightly according to buffer gas pressure, so absorption of the vapor was verified with the lock-in procedure described above. For cells demonstrating very small NMR signal enhancement, a "subtraction average" routine was used to determine the change in NMR signal due to optical pumping. In this procedure, the light was blocked by the shutter for one averaging period and an "off" NMR spectrum was recorded; the light was then unblocked for the same averaging period before an "on" signal was recorded. This cycle was repeated many times, and each set of spectra (on and off) was averaged independently to increase signal-to-noise. Finally the light-on and light-off spectra were subtracted to generate a "difference" NMR spectrum which revealed the effects of the optical pumping light. This procedure was repeated for both transitions to eliminate systematic effects of the light switching (e.g., heating of the cell). Theory predicts the difference signal for the σ− transition should be negative, since the vapor electrons are being pumped into a state which will couple to the energetically unfavorable nuclear state. This will decrease the NMR signal when the light is on, and when the thermal signal is subtracted from it the result will be negative. The opposite will be true for the σ+ transition.

Other cells showed dramatic enhancement of the NMR signal which could be detected without averaging. For these cells no subtraction averaging was used. The experimental preparation and procedure described above serve to list the conditions under which the following results were measured. The general technique of polarizing solid compounds through spin transfer from an optically-pumped alkali vapor can be performed without using the exact steps listed above.

Figure 5A:
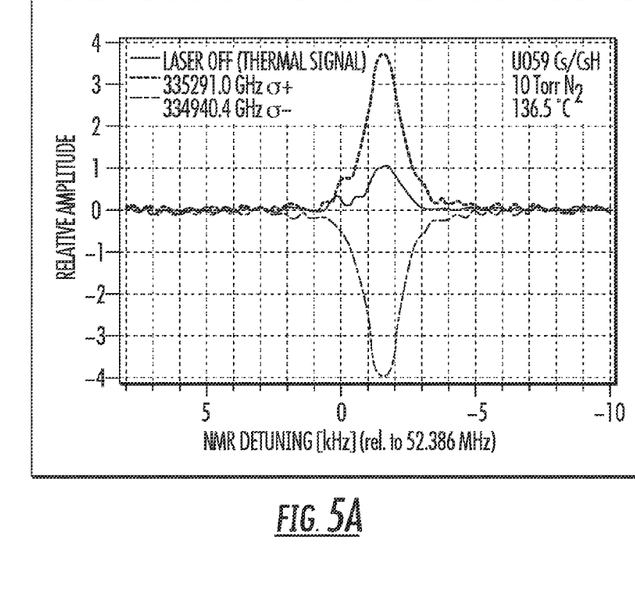
FIG. 5A shows NMR enhancement signals from a cell containing cesium hydride and 11 Torr of $N_2$ gas.
Figure 5B:
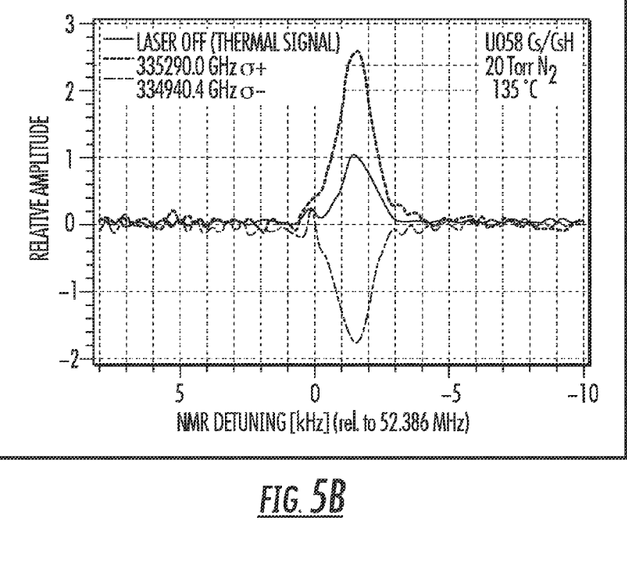
FIG. 5B shows NMR enhancement signals from a cell containing cesium hydride and 20 Torr of $N_2$ gas.

FIGS. 5A-5B show the NMR enhancement signals from two cesium hydride cells. These cells were filled with 11 and 20 Torr of $N_2$ as a quenching gas; the maximum observed NMR signals were 3.97 and 2.57 times the thermal signal, respectively. The maximum enhancement in the 11 Torr case is negative, in the energetically unfavorable sense. The direction of the enhancement is irrelevant to the NMR application.

Figure 6:
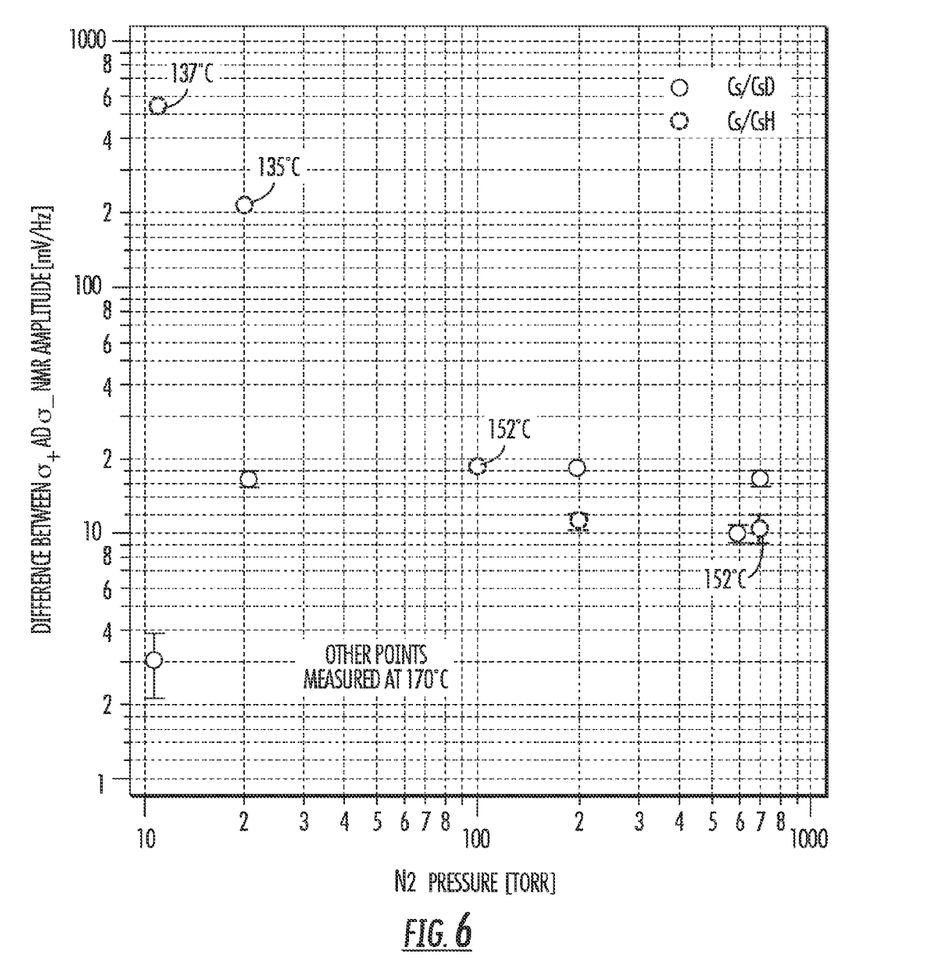
FIG. 6 is a graph of variation of NMR signal change as a function of buffer gas in each cell.

The dependence of the NMR enhancement on buffer gas pressure can be used to determine the mechanism of spin transfer. FIG. 6 shows the maximum enhancement observed in a series of Cs/CsH cells 70 and Cs/CsD cells 72 with varying pressures of $N_2$ buffer gas. The vertical axis reflects the NMR signal induced by optical pumping, defined to be the difference in the NMR signals recorded for the two optical transitions. Accordingly, if optical pumping had no effect, the data points would all have zero difference signal. Thermal equilibrium NMR signals varied among the cells, but the effect of optical pumping is measured by the total amount of spin transferred to the hydride and is thus independent of the thermal signal.

Since the only way to produce nuclear polarization in the vapor is through collisional interactions, it would be expected that the nuclear polarization of the vapor would increase with increasing buffer gas pressure. Accordingly, these data do not support spin transfer mechanisms which rely upon nuclear polarization transfer from the vapor, since the strongest enhancement is seen at very low $N_2$ pressures.

The low enhancement observed in cesium deuteride is still unexplained, but it should be noted that these experiments have demonstrated marked variability in the quality of the optical pumping cells. Accordingly, these data do not preclude the possibility of polarizing alkali compounds beyond the hydrides.

In another experiment, the frequency of the pumping light was scanned through the absorption resonance of the alkali vapor and the CsH NMR enhancement was measured. The enhancement occurred only when the alkali vapor was absorbing the laser light. Because alkali atoms adsorbed on the hydride surface would have strongly-perturbed electron wavefunctions, their absorption spectrum would be much broader than that of free alkali vapor atoms. This indicates that the nuclear polarization enhancement cannot be due to direct optical pumping of surface-adsorbed alkali atoms.

It is to be understood that the above-described embodiments are illustrative of only a few of the many possible specific embodiments, which can represent applications of the principles of the invention. Numerous and varied other arrangements can be readily devised in accordance with these principles by those skilled in the art without departing from the spirit and scope of the invention.

What is claimed is:

1. A method for polarizing a non-gaseous material for use in NMR spectroscopy comprising the steps of:
   providing a cell containing an alkali metal vapor, said non-gaseous material and optionally a buffer gas;
   applying a magnetic field to said cell; and
   pumping resonant laser light through said cell for polarizing said non-gaseous material,
   extracting said polarized non-gaseous compound from said cell; and
   using said polarized non-gaseous compound in vivo or in vitro medical diagnostics or chemical identification, wherein said vapor atoms in said alkali metal vapor are polarized and the vapor atoms transmit spin polarization to said non-gaseous compound.

2. The method of claim 1 wherein said cell is produced with alkali metal further comprising the step of:
   heating said cell to vaporize at least some of said alkali metal to produce said alkali vapor.

3. The method of claim 2 wherein said non-gaseous material is a solid compound of an alkali salt containing a same or different alkali metal than said alkali metal in said cell.

4. The method of claim 1 wherein said non-gaseous material is a solid compound of NaCl, CsH, CsCl, or CsF.

5. The method of claim 1 wherein said buffer gas is nitrogen or hydrogen.

6. The method of claim 1 wherein said resonant laser light is circularly polarized.

7. The method of claim 5 wherein said resonant laser light is at a D1 transition of said alkali vapor.

8. The method of claim 5 wherein said resonant light is at D2 transition of said alkali vapor.

9. The method of claim 1 wherein said magnetic field is a low magnetic field at which electron Zeeman splitting is less than hyperfine splitting for said alkali.

10. The method of claim 1 wherein said magnetic field is a high magnetic field at which electron splitting is larger than hyperfine splitting for said alkali.

11. The method of claim 1 further comprising the step of exposing said cell to microwave power at a frequency near a difference between electron and nuclear Lamor frequencies at the applied magnetic field.

12. The method of claim 1 wherein said medical diagnostic is magnetic resonance imaging.

13. A system for polarizing a non-gaseous material for use in NMR spectroscopy comprising:
   a cell containing an alkali metal vapor, said solid compound and optionally a buffer gas;
   means for applying a magnetic field to said cell; and
   means for polarizing said solid compound by pumping resonant laser light through said cell, wherein said vapor atoms in said alkali vapor are polarized and the vapor atoms transmit spin polarization to said non-gaseous material; and
   means for extracting said polarized material from said cell.

14. The system of claim 13 further comprising:
   means for heating said cell to vaporize at least some of an alkali metal contained in said cell to produce said alkali metal vapor.

15. The system of claim 13 wherein said non-gaseous material is a solid compound of an alkali salt containing the same or different alkali metal than said alkali metal in said cell.

16. The system of claim 13 wherein said non-gaseous material is a solid compound of NaCl, CsH, CsCl, or CsF.

17. The system of claim 13 wherein said buffer gas is nitrogen or hydrogen.

18. The system of claim 13 wherein said resonant laser light is circularly polarized.

19. The system of claim 18 wherein said resonant laser light is at a D1 transition of said alkali vapor.

20. The system of claim 18 wherein said resonant light is at D2 transition of said alkali vapor.

21. The system of claim 13 wherein said means for applying a magnetic field applies a low magnetic field at which electron Zeeman splitting is less than hyperfine splitting for said alkali.

22. The system of claim 13 wherein said means for applying a magnetic field is a high magnetic field at which electron splitting is larger than hyperfine splitting for said alkali.

23. The system of claim 13 further comprising means for exposing said cell to microwave power at a frequency near a difference between electron and nuclear Lamor frequencies at the applied magnetic field.

24. A NMR spectroscopy system comprising the system of claim 13.

25. A medical diagnostic system comprising the system of claim 13.

26. The medical diagnostic system of claim 25 wherein said medical diagnostic system provides magnetic resonance imaging.

27. A method of polarizing a sample of a non-gaseous material for use in NMR spectroscopy comprising the step of:
pumping resonant laser light through a magnetic field containing an alkali metal vapor and said sample, for polarizing nuclear spins of the sample in a magnetic field wherein vapor atoms in said alkali metal vapor are polarized and the vapor atoms transmit spin polarization to said sample.

28. The method of claim 27 wherein said sample is a solid compound of an alkali salt containing a same or different alkali metal than said alkali metal in said alkali metal vapor.

29. The method of claim 27 wherein said resonant laser light is circularly polarized.

30. The method of claim 29 wherein said resonant laser light is at a D1 transition of said alkali vapor.

31. The method of claim 27 further comprising the step of exposing said cell to microwave power at a frequency near a difference between electron and nuclear Lamor frequencies at the applied magnetic field.

32. The method of claim 29 wherein said resonant light is at D2 transition of said alkali vapor.

33. The method of claim 27 wherein said magnetic field is a low magnetic field at which electron Zeeman splitting is less than hyperfine splitting for said alkali.

34. The method of claim 27 wherein said magnetic field is a high magnetic field at which electron splitting is larger than hyperfine splitting for said alkali.

35. A method for performing nuclear magnetic resonance of a sample of a non-gaseous material comprising the step of:
pumping resonant laser light through said magnetic field containing an alkali metal vapor and said sample, for polarizing nuclear spins of the sample in a magnetic field wherein vapor atoms in said alkali metal vapor are polarized and the vapor atoms transmit spin polarization to said sample.

36. The method of claim 35 wherein said resonant laser light is circularly polarized.

37. The method of claim 36 wherein said resonant laser light is at a D1 transition of said alkali vapor.

38. The method of claim 35 wherein said resonant light is at D2 transition of said alkali vapor.

39. The method of claim 35 wherein said magnetic field is a low magnetic field at which electron Zeeman splitting is less than hyperfine splitting for said alkali.

40. The method of claim 35 wherein said magnetic field is a high magnetic field at which electron splitting is larger than hyperfine splitting for said alkali.

41. The method of claim 35 further comprising the step of exposing said cell to microwave power at a frequency near a difference between electron and nuclear Lamor frequencies at the applied magnetic field.

42. A method for performing magnetic resonance imaging of a sample of a non-gaseous material comprising the step of:
pumping resonant laser light through said magnetic field containing an alkali metal vapor and said sample for polarizing nuclear spins of the sample in a magnetic field, wherein vapor atoms in said alkali metal vapor are polarized and the vapor atoms transmit spin polarization to said sample.

43. The method of claim 42 wherein said resonant laser light is circularly polarized.

44. The method of claim 43 wherein said resonant laser light is at a D1 transition of said alkali vapor.

45. The method of claim 42 wherein said resonant light is at D2 transition of said alkali vapor.

46. The method of claim 42 wherein said magnetic field is a low magnetic field at which electron Zeeman splitting is less than hyperfine splitting for said alkali.

47. The method of claim 42 wherein said magnetic field is a high magnetic field at which electron splitting is larger than hyperfine splitting for said alkali.

48. The method of claim 42 further comprising the step of exposing said cell to microwave power at a frequency near a difference between electron and nuclear Lamor frequencies at the applied magnetic field.

* * * * *